United States Patent
Sandberg et al.

(10) Patent No.: US 7,087,401 B2
(45) Date of Patent: Aug. 8, 2006

(54) CULTURE MEDIUM AND METHOD FOR DETECTING THERMONUCLEASE-POSITIVE STAPHYLOCOCCI

(75) Inventors: Gregory P. Sandberg, St. Louis Park, MN (US); Patrick A. Mach, Shorewood, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 591 days.

(21) Appl. No.: 10/177,420

(22) Filed: Jun. 20, 2002

(65) Prior Publication Data

US 2003/0235879 A1 Dec. 25, 2003

(51) Int. Cl.
- *C12Q 1/02* (2006.01)
- *C12Q 1/04* (2006.01)
- *C12Q 1/34* (2006.01)
- *C12Q 1/42* (2006.01)

(52) U.S. Cl. .............. 435/34; 435/18; 435/21; 435/29; 435/283.3; 435/883; 435/975

(58) Field of Classification Search ............. 435/34, 435/29, 21, 18, 288.3, 883, 975
See application file for complete search history.

(56) References Cited

U.S. PATENT DOCUMENTS

| | | | |
|---|---|---|---|
| 4,565,783 A | | 1/1986 | Hansen et al. ............ 435/299 |
| 5,232,838 A | | 8/1993 | Nelson et al. ............ 435/30 |
| 5,443,963 A | * | 8/1995 | Lund ....................... 435/34 |
| 5,635,367 A | * | 6/1997 | Lund ....................... 435/34 |
| 5,837,482 A | * | 11/1998 | Mach et al. ............... 435/34 |
| 6,022,682 A | * | 2/2000 | Mach et al. ............... 435/4 |

* cited by examiner

*Primary Examiner*—Louise Leary
(74) *Attorney, Agent, or Firm*—Nancy M. Lambert; Daniel R. Pastirik

(57) ABSTRACT

The present invention provides a method of detecting thermonuclease-positive staphylococci that does not require inactivation of DNase-positive/TNase-negative bacteria with heat. The method includes (a) providing a culture medium selective for growing staphylococci; (b) inoculating the culture medium with a sample; (c) incubating the inoculated culture medium under conditions effective to promote the growth of staphylococci; (d) providing an indicator system that produces a differentiable, detectable signal in the presence of thermonuclease-positive staphylococci; (e) contacting the indicator system with the inoculated, incubated culture medium, thereby forming a detection assembly; (f) incubating the detection assembly under conditions effective for generating the differentiable, detectable signal; and (g) detecting the detectable signal.

The present invention also provides a culture medium for the selective identification of *Staphylococcus aureus*. The culture medium includes at least one first selective agent that selects for growth of staphylococci; at least one second selective agent for differentiating *Staphylococcus aureus* from other staphylococci; at least one first indicator for indicating the presence of staphylococci; and at least one second indicator for differentially indicating the presence of non-staphylococci bacteria. The present invention also provides a method of selectively identifying *Staphylococcus aureus* in a sample by using the culture medium of the present invention.

48 Claims, 1 Drawing Sheet

CULTURE MEDIUM AND METHOD FOR DETECTING THERMONUCLEASE-POSITIVE STAPHYLOCOCCI

BACKGROUND OF THE INVENTION

Detection of potentially enterotoxigenic staphylococci is an important aspect of food processing, and may be used as a means of screening for indications of contamination during processing and for post-processing contamination. Food sample evaluations for potentially enterotoxigenic staphylococci can serve as a direct indication of the presence of potential pathogenic species in food. The detection of *Staphylococcus aureus* (*S. aureus*), a known enterotoxigenic species, is especially important in food processing. Other potentially enterotoxigenic species of *Staphylococcus* are known and the testing of samples for contamination with these species also may be important. In addition, the testing of patient samples to indicate possible pathogenic staphylococcal infection is of importance in the clinical setting.

One method for testing a sample for the presence of staphylococci includes a thin film culture device that includes a dry, reconstitutable culture medium. The culture medium includes a two-indicator system that provides differential colony staining after about 24–40 hours of incubation. Staphylococci in the sample produce metabolites that react with one indicator, a phosphatase substrate, to produce red or red-violet colonies. Non-staphylococci bacteria produce metabolites that react with the second indicator, a glucopyranoside substrate, to produce blue colonies. This method cannot distinguish between *S. aureus* and other staphylococci.

One current method for detecting *S. aureus* uses Baird-Parker egg yolk-tellurite-pyruvate agar medium (abbreviated as BPA) for determining the presumptive presence of *S. aureus* in a fractional part of a sample. In this method, BPA plates are examined for the presence of "typical" and "a typical" colonies after 48 hours incubation. Samples of the colonies are then transferred to brain heart infusion for an additional incubation of up to 24 hours. The broth cultures are mixed with rabbit plasma for an additional 6–24 hours incubation. The culture-plasma mixtures are then evaluated for the presence of coagulation of the plasma (i.e., clotting). Cultures giving rise to a clot are considered to be coagulase positive. A presumptive positive from BPA followed by a coagulase-positive result is considered to be confirmation of the presence of *S. aureus* in the sample.

The use of coagulase activity associated with the presence of *S. aureus* also has been thought to correlate with potential pathogenicity, including enterotoxin production. The tedious, time-consuming nature of the coagulase test, however, makes it impractical for routine testing of large numbers of samples.

Two alternatives to the coagulase test have shown good statistical relation to the coagulase reaction of *S. aureus*: hyaluronidase and thermostable nuclease (TNase). The hyaluronidase system, however, is complex and costly. Testing for TNase activity was also tedious until Lachica et. al., Applied Microbiology 21(4), pp. 585–87 (1971), described the use of the metachromatic dye, toluidine blue O (TBO), for the detection of TNase by the differential staining in the presence of hydrolyzed and unhydrolyzed DNA.

The TNase detection method has been described and used in methods including (1) forming wells in a TBO/DNA agar-filled petri dish and placing boiled cultures within the well to determine the presence of TNase, (2) forming wells in a TBO/DNA agar medium cast on the surface of a microscope slide (or equivalent) and following the procedure of (1), (3) overlaying a Baird-Parker agar (or equivalent) plate with molten TBO/DNA agar after the developed BPA plate has been pre-incubated at 60° C. for at least 2 hours. (1), (2), and (3) give readable results in 2–4 hours from colonies or suspensions that are positive for TNase. Using these methods, various investigators have shown correlation of the TNase test with the coagulase test for *S. aureus* of up to 100%.

Enterotoxigenic staphylococci also may be detected using an article containing unhydrolyzed nucleotides and toluidine blue O that is adapted for placement against a sample suspected of containing enterotoxigenic staphylococci. The sample must be pre-heated to 60° C. for at least about 30 minutes to inactive non-thermostable nuclease activity. If TNase is present, which correlates to the presence of enterotoxigenic staphylococci, it will hydrolyze nucleotides provided in the article. The hydrolyzed nucleotides will react with the toluidine blue O to produce a detectable red or pink halo surrounding the colony containing the enterotoxigenic staphylococci.

TNase activity also has been detected in other potentially enterotoxigenic *Staphylococcus* species, including some that are coagulase negative.

While some methods of TNase testing are reliable, their utility in testing or screening large numbers of samples is severely limited by the need to form wells or prepare molten agar in order to obtain results, which are time consuming and inefficient techniques in the context of testing large numbers of samples. It would thus be desirable to develop a TNase test for potentially enterotoxigenic staphylococci that would permit efficient and reliable testing or screening of large numbers of samples, in food processing or in clinical applications.

SUMMARY OF THE INVENTION

The present invention provides a novel dry culture medium for the selective identification of *Staphylococcus aureus,* the culture medium including at least one first selective agent that selects for growth of staphylococci; at least one second selective agent for differentiating *Staphylococcus aureus* from other staphylococci; at least one first indicator for indicating the presence of staphylococci; and at least one second indicator for differentially indicating the presence of non-staphylococci bacteria. In some embodiments, the culture medium includes potassium tellurite as a selective agent. In one embodiment, the selective agents include lithium chloride, aztreonam and potassium tellurite.

In another aspect, the present invention provides a thin film bacterial culture device including a dry culture medium capable of selectively identifying *Staphylococcus aureus.*

In another aspect, the present invention provides a method of analyzing a sample for the presence or absence of *Staphylococcus aureus.* The method includes (a) inoculating a culture medium with a sample, the culture medium including at least one first selective agent that selects for growth of staphylococci, at least one second selective agent for differentiating *Staphylococcus aureus* from other staphylococci, at least one first indicator for indicating the presence of staphylococci, and at least one second indicator for differentially indicating the presence of non-staphylococci bacteria; (b) incubating the inoculated culture medium under conditions that permit growth of *Staphylo-*

*coccus aureus*; and (c) inspecting the culture medium to determine whether *Staphylococcus aureus* is present.

Certain embodiments of the method include detecting colonies of *Staphylococcus aureus* by detecting a detectable signal generated by the reaction of phosphatase produced by *Staphylococcus aureus* and an indicator that produces a detectable signal in the presence of phosphatase. In certain embodiments, *Staphylococcus aureus* is detected by detecting red colonies. The method also may include enumeration of *Staphylococcus aureus* in the sample by counting *Staphylococcus aureus* colonies that grow on the culture medium.

In another aspect, the present invention provides a kit for detection and enumeration of *Staphylococcus aureus*. The kit includes (a) nutrients effective for growing staphylococci from a sample; (b) reagents that select for growth of staphylococci; and (c) at least one indicator for indicating the presence of *Staphylococcus aureus*. In some embodiments, the reagents of the kit include potassium tellurite, lithium chloride and aztreonam. In certain embodiments, the indicator includes 5-bromo-6-chloro-3-indolylphosphate or 6-chloro-3-indolylphosphate.

In another aspect, the present invention provides a method of detecting thermonuclease-positive staphylococci. The method includes (a) providing a culture medium selective for growing staphylococci; (b) inoculating the culture medium with a sample; (c) incubating the inoculated culture medium under conditions effective to promote the growth of staphylococci; (d) providing an indicator system that produces a differentiable, detectable signal in the presence of thermonuclease-positive staphylococci; (e) contacting the indicator system with the inoculated, incubated culture medium, thereby forming a detection assembly; (f) incubating the detection assembly under conditions effective for generating the differentiable, detectable signal; and (g) detecting the detectable signal.

In certain embodiments, the step of incubating the detection assembly is performed at temperatures less than 60° C. at least until the detectable signal is detected. In some embodiments, the detection assembly is incubated at temperatures less than about 42° C. In one embodiment, the detection assembly is incubated at a temperature of about 37° C.

In certain embodiments, detecting the detectable signal includes detecting colonies that have a pink halo. The method also may include enumeration of thermonuclease-positive staphylococci in the sample by counting colonies of thermonuclease-positive staphylococci that grow on the culture medium.

In another aspect, the present invention also provides a kit for detection and enumeration of thermonuclease-positive staphylococci. The kit includes (a) nutrients effective for growing staphylococci from a sample; (b) reagents that select for growth of thermonuclease-positive staphylococci; and (c) an indicator system for indicating the presence of thermonuclease-positive staphylococci in a sample.

In some embodiments, the reagents in the kit include potassium tellurite, lithium chloride and aztreonam. In some embodiments, the indicator system of the kit includes toluidine blue O and unhydrolyzed nucleotides.

DETAILED DESCRIPTION OF ILLUSTRATIVE EMBODIMENTS OF THE INVENTION

Figure 1:
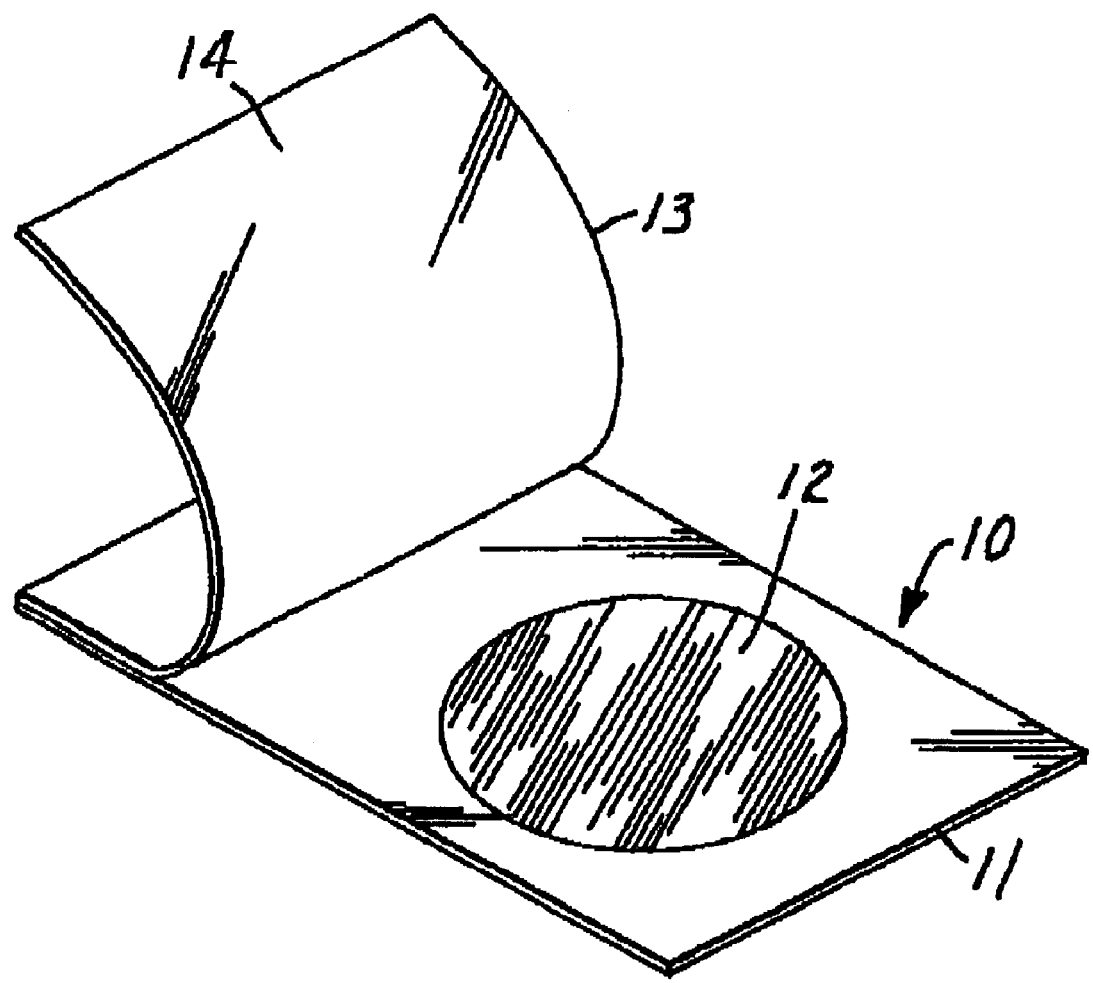
FIG. 1 is a top perspective view of an exemplary embodiment of a thin-film culture plate device.

Prior methods of detecting *S. aureus* typically include a confirmation step such as a coagulase test, TNase detection, or hyaluronidase test to confirm the presence of *S. aureus*. As described above, some methods require a confirmation test after an initial incubation period of up to 48 hours. The culture medium of the present invention may provide an affirmative result indicating the presence of *S. aureus* in as little as 18 hours, without a confirmatory second step.

The dry culture medium of the present invention may be included in a thin film culture media device. Such devices provide a convenient platform for growing microbial cultures. Suitable devices are described in U.S. Pat. Nos. 4,565,783, issued Jan. 21, 1986; 5,232,838, issued Aug. 3, 1993; and 5,443,963, issued Aug. 22, 1995. The culture medium includes a novel combination of selective agents and indicators that permit the positive identification of *S. aureus* in a sample without resorting to a confirmatory step in as little as 18 hours, typically about 24 hours.

FIG. 1 illustrates an exemplary embodiment of a thin film culture plate device. FIG. 1 shows an example of a thin film culture plate device 10 suitable for use in the invention. The device contains a self-supporting substrate 11, such as a film, to which a dried culture medium 12 is adhered. The culture medium may include, for example, medium adapted for growing staphylococci coated onto film as dried broth, or as powdered nutrients. A cover film 13 (shown peeled away from the substrate 11) covers the culture medium 12 during storage and incubation. The cover film 13 preferably contains a gelling agent coated an a surface 14 that contacts the culture medium 12. Upon application of a test sample to the culture medium 12, the cover film 13 is applied over the self-supporting substrate 11 to contact the gelling agent with the sample and culture medium 13. The device is then incubated to allow microorganisms present in the sample to multiply and form colonies on the gelled culture medium.

The culture medium of the present invention may include nutrients, salts and ions generally suitable for promoting the growth of staphylococci colonies when the culture medium is inoculated with a sample containing staphylococci and the inoculated culture medium is incubated under suitable conditions. The culture medium also may include one or more gelling agents. Suitable nutrients, salts, ions, and gelling agents are described in U.S. Pat. No. 5,443,963.

The culture medium of the present invention includes at least one selective agent that selects for growth of staphylococci. The selection of staphylococci may include inhibiting the growth of non-staphylococci bacteria, promoting the growth of staphylococci, or both. The promoting the staphylococci growth provided by the at least one first selective agent may be direct, indirect (e.g., by reducing competition for nutrients by inhibiting non-staphylococci), or both.

Any element, radical, ion, or compound that selects for the growth of staphylococci may be suitable for use as a selective agent. Suitable selective agents include but are not limited to lithium chloride, aztreonam, potassium tellurite, sodium chloride, nalidixic acid, colistin methanesulfonate, glycine-hydrochloride, potassium thiocyanate, sodium azide, polymyxin B, sulfamethazine, an antibiotic, and any combination of any of the foregoing.

Certain selective agents may not only select for the growth of staphylococci, but also may differentially select for growth of *S. aureus* over other staphylococci under certain conditions. For example, a culture medium that includes potassium tellurite and egg yolk is capable of selectively differentiating *S. aureus* from all other bacterial species. Egg yolk is commercially available either as an emulsion or in a dehydrated form.

A dry culture medium according to the present invention may be applied to one or more surfaces of a thin film culture device in the following manner. The components of the culture medium may be dissolved in a solvent. The resulting solution may then be coated onto one or more surfaces of the culture device. The coating is then allowed to dry, leaving the dried culture medium on the surfaces of the device that had been coated with the culture medium solution. The coating may be dried in any suitable manner including but not limited to air drying and heating.

The quantity of each component of the dry culture medium is at least partially determined by at least two factors: (1) the concentration of that component in the culture medium solution, and (2) the amount of the solution coated onto a surface of the culture device (the coating weight). Suitable coating weights may range from about 0.45 mg/cm$^2$ to about 2.5 mg/cm$^2$. In some embodiments, the culture medium nutrients may be coated separately from the indicators. In such embodiments, the coating weight for the culture medium nutrients may range from about 1.6 mg/cm$^2$ to about 2.5 mg/cm$^2$. In one embodiment, the coating weight of the nutrient coating is about 2.1 mg/cm$^2$. The coating weight for the indicator coating may range from about 0.45 mg/cm$^2$ to about 0.84 mg/cm$^2$. In one embodiment, the coating weight of the indicator coating is about 0.62 mg/cm$^2$.

The amount of the selective agent included in the culture medium may depend, in part, upon the particular selective agent or combination of selective agents chosen for use in a particular culture medium. For example, in one embodiment, the culture medium includes lithium chloride, aztreonam, and potassium tellurite as selective agents. In the context of the coating weights described above for a nutrient coating, lithium chloride may be included in the coating solution in an amount that ranges from about 5 g/L to about 15 g/L. In one embodiment, the coating solution includes 10 g/L of lithium chloride before being coated onto the culture device. Similarly, aztreonam may be included in an amount that ranges from about 0.001 g/L to about 0.015 g/L. In one embodiment, the coating solution includes 0.01 g/L of aztreonam. Potassium tellurite may be included in an amount that ranges from about 0.1 g/L to about 0.19 g/L. In one embodiment, the culture medium includes 0.16 g/L of potassium tellurite.

The culture medium of the present invention also includes at least one first indicator for indicating the presence of staphylococci. The first indicator may include any suitable indicator that permits differentiation of staphylococci and non-staphylococci. In some embodiments, the first indicator includes a phosphatase substrate. The indicator may react with phosphatase produced by staphylococci to produce a detectable signal. The detectable signal may include the generation of a precipitable substrate that produces a detectable color change. For example, commercially available indicators include 5-bromo-6-chloro-3-indolylphosphate or 6-chloro-3-indolylphosphate, each of which may react with staphylococcus phosphatase to produce a red to red-violet colored, precipitated substrate. In the context of the coating weights described above for an indicator coating, the first indicator may be included in the coating solution in an amount that ranges from about 0.34 g/L to about 0.54 g/L. In certain embodiments, the culture medium includes about 0.44 g/L of 5-bromo-6-chloro-3-indolylphosphate.

The culture medium of the present invention also includes at least one second indicator for indicating the presence of non-staphylococci bacteria. The second indicator may include any indicator that provides a detectable signal in the presence of non-staphylococci, but does not interact with staphylococci. For example, certain glucopyranosides react with β-glucosidase produced by many bacteria (not including staphylococci) to produce a detectable signal, such as generation of a blue signal. Suitable β-glucosidase indicators include but are not limited to 5-bromo-4-chloro-3-indolyl-β-D-glucopyranoside. In the context of the coating weights described above for an indicator coating, the second indicator may be included in the culture medium in an amount that ranges from about 0.1 g/L to about 0.3 g/L. In certain embodiments, the culture medium includes about 0.2 g/L of 5-bromo-4-chloro-3-indolyl-β-D-glucopyranoside.

The culture medium of the present invention also may be suitable for use in liquid, semi-solid, or solid culture media. The concentrations of ingredients provided in the context of the coating solution described above may be suitable for use as a liquid culture medium or, alternatively, a semi-solid or solid culture medium with the addition of a gelling agent. This is surprising because the converse is not always true, i.e., a dried form of a known liquid culture medium does not necessarily perform adequately in connection with a dry culture device such as that described in U.S. Pat. No. 4,565,783.

The culture medium of the present invention permits the affirmative, differentiated identification of *S. aureus* in a sample without a confirmatory second step. Accordingly, the present invention provides a method for analyzing a sample for the presence or absence of *S. aureus*. The differential, affirmative identification of *S. aureus* in a sample is possible if one of the selective agents included in the culture medium selectively differentiates between *S. aureus* and other staphylococci. One selective agent that provides such a capability is potassium tellurite in combination with egg yolk.

In one embodiment of the method of the present invention, the culture medium includes (a) one or more selective agents that generally select for growth of staphylococci, such as lithium chloride and aztreonam, and (b) potassium tellurite with egg yolk, which permits differentiation between the growth of *S. aureus* and other staphylococci. The selective agents may inhibit the growth of non-staphylococci and, therefore, promote the growth of staphylococci—including *S. aureus*—in the sample by reducing competition for nutrients in the inoculated culture medium. This may result, for example, in larger, more easily detectable colonies if the sample is cultured onto a solid or semi-solid culture medium that permits the growth of individual bacterial colonies.

The culture medium includes at least one first indicator that selectively indicates the presence of staphylococci. Suitable first indicators include the phosphatase substrate indicator described above. In one embodiment, the culture medium includes 5-bromo-6-chloro-3-indolylphosphate or 6-chloro-3-indolylphosphate. The culture medium also may include one or more second indicators that selectively indicate the presence of non-staphylococci. Suitable second indicators include the glucopyranoside indicators described above. In one embodiment, the culture medium includes 5-bromo-4-chloro-3-indolyl-β-D-glucopyranoside.

Method of Detecting *Staphylococcus aureus*

The culture medium is inoculated with a sample. The sample may be from any source including but not limited to food, living or dead animal or plant tissue, water, air, other inanimate environmental surfaces, and human clinical sources. If the source of the sample is solid, the sample may be suspended in a liquid diluent prior to inoculation of the culture medium. Also, a liquid or liquefied sample may be diluted prior to inoculating the culture medium. In certain embodiments, the sample may be serially diluted and the serial dilutions used to inoculate a plurality of culture media in order to obtain a more precise enumeration of S. aureus in the original sample.

The inoculated culture medium is incubated under conditions that permit the growth of staphylococci. In one embodiment of the method of the present invention, the inoculated culture medium is incubated at 37° C. for about 24 hours. However, in other embodiments, the inoculated culture medium may be incubated from about 18 hours to about 48 hours at about 30° C. to about 42° C.

As described above, phosphatase substrate indicators may react with phosphatase produced by staphylococci to produce red to red-violet color. When used in combination with a solid or semi-solid culture medium—e.g., agar—red to red-violet colonies of staphylococci become visible. In the method of the present invention, a combination of selective agents that includes potassium tellurite permits differentiation of S. aureus from other staphylococci by selectively inhibiting growth of non-S. aureus staphylococci so that only S. aureus grow sufficiently to produce sufficient phosphatase to react with the indicator to generate the red color.

In some embodiments of the method of the present invention, the S. aureus present in the sample may be enumerated. One may enumerate the S. aureus in a sample by selecting a form of culture medium that permits the formation of colonies. After the culture medium is inoculated and incubated under conditions that permit colonies of S. aureus to form, the colonies may be counted. Colonies may be counted by counting the detectable signal generated by reaction of the indicator and phosphatase produced by the S. aureus. In embodiments in which the phosphatase substrate indicators 5-bromo-6-chloro-3-indolylphosphate or 6-chloro-3-indolylphosphate are employed, the detectable signal may include red to red-violet colored colonies. Thus, in certain embodiments, enumeration of S. aureus includes merely counting the red to red-violet colonies.

Alternatively, the detectable signal generated by the reaction of a phosphatase substrate and phosphatase from the S. aureus may include any other suitable type of detectable signal. Suitable detectable signals include but are not limited to a chemiluminescent signal, a fluorescent signal, or a change in electrical conductivity. In some embodiments, detection of the detectable signal may be accomplished manually, while in other embodiments detection of the detectable signal may require specialized detection instrumentation known to those of ordinary skill in the art. The method used to enumerate S. aureus in a particular sample may depend, at least in part, on the type of detectable signal used in the method of the present invention.

Some embodiments of the method of the present invention may employ a series of serial dilutions in order to more precisely enumerate S. aureus in a sample. Not all applications of the method of the present invention will require the precision offered by serial dilutions, however. Serial dilutions, when desired, may be employed regardless of the particular detectable signal used in a given assay.

Method of Detecting Thermonuclease-positive Staphylococci

Certain embodiments of the culture medium of the present invention may be used to detect staphylococci that produce thermostable nuclease (TNase). As described above, TNase production is a generally accepted indicator of enterotoxigenic staphylococci. Thus, an accurate TNase assay may provide an accurate assay for detecting enterotoxigenic staphylococci including certain strains of each of S. aureus, S. intermedius, S. hyicus.

Current methods for detecting TNase-positive staphylococci require a step in which bacteria that produce DNase that is not thermostable (DNase-positive/TNase-negative bacteria) are inactivated by heating the culture, typically to temperatures of at least about 60° C. Certain embodiments of the culture medium of the present invention permit detection of TNase-positive staphylococci by a method that does not require inactivation of DNase-positive/TNase-negative bacteria by heating. Thus, the present invention may provide a rapid and accurate assay for detecting TNase-positive staphylococci without the additional time, labor, and equipment that is required to inactivate DNase-positive/TNase-negative bacteria with heat. Also, because the bacteria are not subject to the stress of the heating step, the method of detecting TNase-positive staphylococci of the present invention may provide healthier TNase-positive colonies that may be picked and cultured for further characterization, if desired.

The method includes providing a culture medium that is selective for growing staphylococci. The culture medium may include one or more selective agents that selects for growth of staphylococci. Suitable selective agents include but are not limited to those listed above as suitable for use as the first selective agent in the culture medium of the present invention. In some embodiments, the culture medium includes a combination of selective agents including potassium tellurite. In one embodiment, the culture medium includes lithium chloride, aztreonam and potassium tellurite.

In some embodiments, the culture medium includes one or more indicators that may indicate the presence of staphylococci or non-staphylococci when the culture medium is inoculated with sample and then incubated under suitable conditions. Suitable indicators include but are not limited to those described above as suitable for use in the method of detecting S. aureus according to the present invention.

The inoculated culture medium is incubated under conditions that promote growth of staphylococci. Suitable conditions include those incubation time and incubation temperature conditions described above for the method of detecting S. aureus according to the present invention.

Next, an indicator system is contacted with at least a portion of the inoculated and incubated culture medium, thereby forming a detection assembly. The indicator system includes at least one reagent that, when in contact with culture medium that includes TNase-positive staphylococci and DNase-positive/TNase-negative bacteria, produces a TNase-positive-specific, detectable signal. In some embodiment, the indicator system includes toluidine blue O and unhydrolyzed nucleotides. In one embodiment, the indicator system includes an article that includes toluidine blue O, unhydrolyzed nucleotides, and a binder, such as the article described in U.S. Pat. No. 6,022,682, issued Feb. 8, 2000.

The detection assembly is incubated under conditions that permit TNase to react with the unhydrolyzed nucleotides in the indicator system, thereby generating a detectable signal. In some embodiments, the detection assembly is incubated at a temperature ranging from about 4° C. to about 42° C. In some embodiments, the detection assembly is incubated at about 37° C. The detection assembly may be incubated from about 1 minute to about 48 hours. In some embodiments, the detection assembly is incubated from about 1 hour to about 3 hours. In one embodiment, the detection assembly is incubated at about 37° C. for about 1 hour.

In the method of detecting TNase-positive staphylococci according to the present invention, the indicator system generates a detectable signal for TNase-positive staphylococci but does not generate a detectable signal for DNase-positive/TNase-negative bacteria, even in the absence of a step in which DNase-positive/TNase-negative bacteria are inactivated with heat. DNase-positive/TNase-negative bacteria may be sufficiently stressed by one or more selective agents in the culture medium that colonies of DNase-positive/TNase-negative bacteria cannot produce enough non-thermostable nuclease to generate a detectable signal when contacted with the detection system. Only TNase-positive staphylococci are able to produce sufficient nuclease (i.e., TNase) to generate a detectable signal when contacted with the detection system. In some embodiments, the DNase-positive/TNase-negative bacteria are stressed, in particular, by certain combinations of selective agents in the culture medium. One useful combination of selective agents includes aztreonam, lithium chloride and potassium tellurite.

Thus, methods according to the present invention may provide rapid and accurate detection of TNase-positive staphylococci without having to inactivate DNase-positive/TNase-negative bacteria with heat. In other words, the methods of the present invention permit the detection of TNase-positive staphylococci without having to incubate the detection assembly at temperatures of at least about 60° C. In some embodiments, the method may be performed while maintaining the temperature of the detection assembly at less than about 40° C. In one embodiment, the method is performed while maintaining the temperature of the detection assembly at about 37° C.

TNase-positive staphylococci are detected by detecting the detectable signal. In embodiments in which the detection system includes toluidine blue O and unhydrolyzed nucleotides, detecting TNase-positive staphylococci may include detecting colonies that have pink halos. TNase-positive staphylococci may be enumerated using strategies described above for enumerating S. aureus.

The present invention also provides a kit for the detection, enumeration, or both, of S. aureus. The kit includes nutrients effective for growing staphylococci, at least one first selective agent for selecting the growth of staphylococci, at least one second selective agent for differentiating S. aureus from other staphylococci, and an indicator that differentially indicates that presence of staphylococci. In some embodiments, the kit includes a thin film culture device such as that described in U.S. Pat. No. 4,565,783 or U.S. Pat. No. 5,232,838. In some embodiments, the kit includes potassium tellurite as a first selective agent, a second selective agent, or both. In one embodiment, the kit includes potassium tellurite, lithium chloride and aztreonam as selective agents. In some embodiments, the kit includes a phosphatase substrate as the indicator. In one embodiment, the indicator includes 5-bromo-6-chloro-3-indolylphosphate or 6-chloro-3-indolylphosphate. The kit may further include additional components, if desired, selected to permit use of the kit for one or more particular applications.

The present invention also provides a kit for the detection, enumeration, or both, of TNase-positive staphylococci. The kit includes nutrients effective for growing staphylococci, at least one selective agent for selecting the growth of TNase-positive staphylococci, and an indicator system for indicating the presence of TNase-positive staphylococci. In some embodiments, the kit includes a thin film culture device such as that described in U.S. Pat. No. 4,565,783 or U.S. Pat. No. 5,232,838. In some embodiments, the kit includes potassium tellurite as a selective agent. In one embodiment, the kit includes potassium tellurite, lithium chloride and aztreonam as selective agents. In some embodiments, the kit includes an indicator system such as that described in U.S. Pat. No. 6,022,682. In one embodiment, the indicator system includes toluidine blue O and unhydrolyzed nucleotides. The kit may further include additional components, if desired, selected to permit use of the kit for one or more particular applications.

EXAMPLES

The following examples have been selected merely to further illustrate features, advantages, and other details of the invention. The particular materials and amounts used as well as other conditions and details are not to be construed in a matter that would unduly limit the scope of this invention, however. Unless otherwise indicated, all parts and percentages are by weight and all molecular weights are weight average molecular weight.

| Abbreviations, Descriptions, and Sources of Materials | | |
| --- | --- | --- |
| Abbreviation | Description | Source |
| BCIG | 5-Bromo-4-chloro-3-indoxyl-beta-glucopyranoside | Biosynth International, Naperville, IL |
| BCIP | 5-Bromo-6-chloro-3-indoxyl phosphate disodium salt | Biosynth International |
| TBO | Toluidine blue O | Sigma-Aldrich, St. Louis, MO |

Starting Preparations

Baird-Parker Agar (BPA) Preparation: A sample (63 g) of BPA powder (Becton Dickinson, Sparks, Md.) was added to 950 ml of reverse osmosis water, heated to boiling for one minute to dissolve the powder, autoclaved at 121° C. for 15 minutes, and cooled to 45–50° C. A 50-ml aliquot of egg yolk tellurite solution (Becton Dickinson) was added and the resulting solution mixed thoroughly and poured into sterile Petri dishes. The agar was then allowed to solidify to yield the BPA Preparation.

Example 1

Preparation of Selective Culture Medium

A culture medium selective for growing staphylococci and capable of differentiating *Staphylococcus aureus* from other staphylococci was prepared by initially combining the ingredients shown in Table 1 at the designated concentrations in 1 liter of deionized water. The resulting suspension was mixed with constant stirring with an air mixer (with vigorous vortex), heated to 80° C., allowed to cool to room temperature, and then refrigerated overnight at 4° C.

TABLE 1

| Composition of Selective Culture Medium | |
| --- | --- |
| Ingredient | Concentration (grams/liter) |
| Enriched Casein Peptone (Remel, Lenexa, KS) | 15.0 |
| Standard Casein Peptone (Remel) | 5.0 |
| Yeast Extract (Remel) | 10.0 |
| Sodium Pyruvate (Sigma-Aldrich) | 40.0 |
| Lithium Chloride (Sigma-Aldrich) | 10.0 |
| BCIP Indicator (Biosynth Int.) | 0.44 |
| BCIG Indicator (Biosynth Int.) | 0.2 |
| Aztreonam (Bristol Myers Squibb, Syracuse, NY) | 0.01 |
| Potassium Tellurite (Sigma-Aldrich) | 0.16 |

TABLE 1-continued

Composition of Selective Culture Medium

| Ingredient | Concentration (grams/liter) |
| --- | --- |
| Egg Yolk Enrichment 50% (Difco Laboratories, Detroit, MI) | 50 ml/liter |
| M150 Guar/Xanthan Gum (Rhodia, Cranbury, NJ) | 12.0 |

Example 2

Preparation of Thin-Film Culture Plate with Selective Culture Medium

A thin-film culture plate (similar to PETRIFILM-type plates manufactured by 3M Company, St. Paul, Minn.) was prepared by the following method. The cooled selective culture medium of Example 1 was knife coated onto a sheet of 0.18-mm polyester film at a coating weight of 2.1 mg/cm$^2$. Coated films were heat dried for 2–10 minutes at 93° C. and subsequently laminated to a sheet of 0.5-mm polystyrene foam using an acrylic acid-based adhesive. The resulting laminate was cut into a 7.6-cm×10.2-cm rectangle and a 5-cm diameter disk was cut from the center of the polystyrene foam layer to provide a well for subsequent placement of a test sample. A top film for the Culture Plate was prepared by coating an adhesive and guar gum powder as described in U.S. Pat. No. 6,022,682 (but excluding the TTC indicator) onto a 0.1-mm sheet of polypropylene. The coated polypropylene sheet was then cut into a 7.6-cm×10.2-cm rectangle and fastened to the coated polyester-foam laminate rectangle using a double-sided adhesive tape as a hinge, such that the coated-side of the top film faced the open well and covered the entire surface of the laminate. Thin-film culture plates prepared in this way were designated as SEP Plates.

Example 3

Preparation of Verification Disk

A detection medium used in the preparation of articles (e.g., verification disks) for detection of *Staphylococcus aureus* and other thermonuclease-positive staphylococci was prepared by initially combining all of the ingredients shown in Table 2 (except the TBO and guar gum) at the designated concentrations in 1 liter of deionized water. The resulting suspension (pH between about 8.8 and 9.6) was mixed with constant stirring and heated to boiling. The TBO was added to the mixture and the heat source was removed while maintaining the stirring. The hot suspension was then mixed with an air mixer (with vigorous vortex), the guar gum was added, and the mixing was continued to afford a uniform suspension that was then refrigerated overnight at 4° C.

TABLE 2

Composition of Detection Medium

| Ingredient | Concentration (grams/liter) |
| --- | --- |
| Carrageenan (Lamba) (Sigma-Aldrich) | 0.25 |
| DNA (Difco Laboratories) | 3.5 |
| Trizma Base (Sigma-Aldrich) | 32.7 |

TABLE 2-continued

Composition of Detection Medium

| Ingredient | Concentration (grams/liter) |
| --- | --- |
| Trizma HCL (Sigma-Aldrich) | 7.6 |
| Calcium Chloride (Sigma-Aldrich) | 8.0 |
| TBO (Sigma-Aldrich) | 0.2 |
| M150 Guar (Rhodia) | 12.0 |

The above cooled detection medium was knife coated onto a sheet of 0.18-mm polyester film at a coating weight of 0.62 mg/cm$^2$. Coated films were heat dried for 2–10 minutes at 93° C. and cut into 6.0-cm diameter disks.

Example 4

Detection of Bacteria (Pure Strains)

The detection of pure strains of bacteria was carried out by the following five procedures:

Procedure A (PETRIFILM AC Plates): Overnight (35° C.) Tryptic Soy Broth (Remel) cultures of *S. aureus* isolates were diluted into Tryptone Salt Buffer (Sanofi Diagnostics, France; concentration of 9.5 g of Buffer per liter of reverse osmosis water) to approximately 50 colony forming units (cfu)/ml and cultures of non-*S. aureus* isolates were diluted into Tryptone Salt Buffer to approximately 500 cfu/ml. Samples (1 ml) of the diluted cultures were plated onto a PETRIFILM Aerobic Count (AC) Plate (3M Company, St. Paul, Minn.) and incubated at 37° C. for 24 hours. The plates were then visually observed and the number of red colonies (from reaction with the triphenyl tetrazolium chloride (TTC) indicator) was counted. Results are reported in Table 3 (for non-*S. aureus* pure cultures) and in Table 4 (for *S. aureus* pure cultures).

Procedure B (Baird Parker Agar): Samples (0.3–0.4 ml) of the diluted cultures (as described in Procedure A) were plated onto a Baird-Parker Agar Preparation (as described herein) and incubated uninverted at 37° C. for 1 hour to allow the agar to absorb the inoculum and incubated inverted at 37° C. for an additional 47 hours. The plates were then visually observed (as described, for example, in U.S. Pat. No. 5,837,482 (Mach et al.)) and the number typical colonies, non-typical colonies with black precipitate, and non-typical colonies with blue-green precipitate with or without black precipitate were counted. Colonies presumptive positive are then tested for coagulase activity according to standard methodology. The coagulase-positive colonies were considered to confirm the presence of *S. aureus* in the sample. Results (average of 6 replicates per bacterium) are reported in Table 3 (for non-*S. aureus* pure cultures) and in Table 4 (for *S. aureus* pure cultures).

Procedure C1 (SEP Plates without 60° C.-Heating Step and without Verification Disk): A sample (1 ml) of the diluted culture (as described in Procedure A) was dispensed by pipette into the well of a SEP Plate (prepared as described in Example 2). After dispensing, the top film was lowered and gentle pressure (using a spreader) was applied to the top film so that the sample was distributed uniformly in the well. The sample gelled after a minute and the inoculated SEP Plate was then incubated at 37° C. for 24 hours. The plates were then visually observed and the number of red-violet colonies (from reaction with the BCIP indicator), blue-green colonies (from reaction with the BCIG indicator), and black colonies (from reaction with the potassium tellurite) were counted. Results (red-violet colony counts only) are reported in Table 3 (for non-*S. aureus* pure cultures) and in Table 4 (for *S. aureus* pure cultures).

Procedure C2 (SEP Plate without 60° C.-Heating Step and with Verification Disk): A SEP Plate was inoculated with a sample and incubated at 37° C. for 24 hours as described in Procedure C1. The top film was then lifted and a Verification Disk (prepared as described in Example 3) was placed onto the well in the center of the plate. The top film was then lowered and gentle finger pressure applied to the top of the film to ensure that there was complete contact of the disk with the incubated sample. The Plate was reincubated for at 37° C. for 3 hours and the number of pink halos (indicating the enzymatic hydrolysis of DNA, e.g. by DNase or TNase). Results are reported in Table 3 (for non-*S. aureus* pure cultures) and in Table 4 (for *S. aureus* pure cultures).

Procedure C3 (SEP Plate with 60° C.-Heating Step and with Verification Disk): This procedure was carried out exactly like Procedure C2, except that following the initial incubation at 37° C. for 24 hours and before adding the Verification Disk, the SEP Plate was heated at 60° C. for 1 hour. Colonies having pink halos were counted. Results are reported in Table 3 (for non-*S. aureus* pure cultures) and in Table 4 (for *S. aureus* pure cultures).

Assessment of Results: Table 3 compares the counts from the five Procedures for 65 pure cultures containing non-*S. aureus* bacteria. Four strains were positive using Procedure C2 and negative using Procedure B. One strain was negative using Procedure C2, but positive using Procedure B. One strain was positive using both Procedure C2 and Procedure B. Two strains were positive using Procedure C3 and negative using Procedure B. One strain was negative using Procedure C3, but positive using Procedure B. One strain was positive using both Procedure C2 and Procedure B.

Table 4 compares the counts from the five Procedures for 45 *S. aureus* pure cultures. Two strains gave results that were significantly different when comparing the counts from Procedure C1 and Procedure B, three strains gave significantly different counts between Procedure C2 and Procedure B, and one strain gave significantly different counts between Procedure C3 and Procedure B.

Table 5 compares the results of the 110 pure cultures of bacteria using Procedures B and C2. Procedure C2 had sensitivity and specificity of 98% and 94%, respectively. Table 5 also compares the results of the 110 pure cultures of bacteria using Procedures B and C3. Procedure C3 had sensitivity and specificity of 98% and 97%, respectively.

TABLE 3

Counts of Non-*S. aureus* Pure Cultures Using Various Detection Procedures

| Organism | Average Counts for Indicated Procedure | | | | |
|---|---|---|---|---|---|
| | A | B | C1 | C2 | C3 |
| *Bacillus circulans* ATCC 61 | TNTC[a] | 0 | 0 | 0 | 0 |
| *Bacillus* species S 1533 | TNTC | 0 | 0 | 0 | 0 |
| *Bacillus* species Dean | 204 | 0 | 0 | 0 | 0 |
| *Enterococcus durans* ATCC 11576 | 151 | 0 | 0 | 0 | 0 |
| *Enterococcus faecalis* ATCC 14506 | TNTC | 0 | 0 | 0 | 0 |
| *Enterococcus faecalis* M34 | 231 | 0 | 0 | 0 | 0 |
| *Enterococcus faecalis* P89 | TNTC | 0 | 0 | 0 | 0 |
| *Enterococcus faecalis* P90 | TNTC | 0 | 0 | 0 | 0 |
| *Enterococcus faecalis* P91 | TNTC | 0 | 0 | 0 | 0 |
| *Enterococcus faecium* ATCC 6569 | 328 | 0 | 0 | 0 | 0 |
| *Escherichia coli* DG149 | TNTC | 0 | 0 | 0 | 0 |
| *Listeria monocytogenes* ATCC 15313 | 355 | 0 | 0 | 0 | 0 |
| *Serratia liquifaciens* C1 | 264 | 0 | 0 | 0 | 0 |
| *Staphylococcus carnosus* ATCC 51365 | 111 | 0 | 0 | 0 | 0 |
| *Staphylococcus carnosus* S 1549 | 9 | 0 | 0 | 0 | 0 |
| *Staphylococcus cohnii* S 1515 | 292 | 0 | 0 | 0 | 0 |
| *Staphylococcus cohnii* ATCC 35662 | TNTC | 0 | 0 | 0 | 0 |
| *Staphylococcus cohnii* PK 19d | 80 | 0 | 0 | 0 | 0 |
| *Staphylococcus cohnii* PK 20b | 247 | 0 | 0 | 0 | 0 |
| *Staphylococcus epidermidis* S 1539 | 219 | 0 | 0 | 0 | 0 |
| *Staphylococcus epidermidis* S 1542 | TNTC | 0 | 0 | 0 | 0 |
| *Staphylococcus epidermidis* S 1546 | TNTC | 0 | 0 | 0 | 0 |
| *Staphylococcus epidermidis* S 1547 | 216 | 0 | 0 | 0 | 0 |
| *Staphylococcus epidermidis* S 1548 | TNTC | 0 | 0 | 0 | 0 |
| *Staphylococcus epidermidis* ATCC 14990 | TNTC | 0 | 0 | 0 | 0 |
| *Staphylococcus hominis* S 1544 | TNTC | 0 | 0 | 0 | 0 |
| *Staphylococcus hominis* PK 7s | TNTC | 0 | 0 | 0 | 0 |
| *Staphylococcus hominis* S 1523 | 83 | 0 | 0 | 0 | 0 |
| *Staphylococcus hominis* S 1572 | 227 | 0 | 0 | 0 | 0 |
| *Staphylococcus hominis* S 1574 | TNTC | 0 | 0 | 0 | 0 |
| *Staphylococcus hominis* S 1580 | 17 | 0 | 0 | 0 | 0 |
| *Staphylococcus hominis* S 1582 | TNTC | 0 | 0 | 0 | 0 |
| *Staphylococcus hominis* S 1591 | 55 | 0 | 0 | 0 | 0 |
| *Staphylococcus hominis* S 1597 | 41 | 0 | 0 | 0 | 0 |
| *Staphylococcus hyicus* PK 2c | 348 | 0 | NR[b] | 76[d] | 0 |
| *Staphylococcus hyicus* PK 16b | TNTC | 0 | NR | 55[d] | 54[e] |
| *Staphylococcus intermedius* ATCC 29663 | TNTC | 0 | 0 | 0 | 0 |
| *Staphylococcus kloosii* ATCC 43959 | TNTC | 0 | 0 | 0 | 0 |
| *Staphylococcus saprophyticus* S 1510 | TNTC | 0 | 0 | 0 | 0 |
| *Staphylococcus saprophyticus* S 1532 | 146 | 0 | 0 | 0 | 0 |
| *Staphylococcus saprophyticus* S 1534 | TNTC | 0 | 0 | 0 | 0 |

TABLE 3-continued

Counts of Non-*S. aureus* Pure Cultures Using Various Detection Procedures

| | Average Counts for Indicated Procedure | | | | |
|---|---|---|---|---|---|
| Organism | A | B | C1 | C2 | C3 |
| *Staphylococcus saprophyticus* S 1535 | TNTC | 0 | 0 | 0 | 0 |
| *Staphylococcus saprophyticus* S 1541 | 80 | 0 | 0 | 0 | 0 |
| *Staphylococcus saprophyticus* S 1545 | TNTC | 0 | 0 | 0 | 0 |
| *Staphylococcus saprophyticus* S 1509 | TNTC | 0 | 0 | 0 | 0 |
| *Staphylococcus saprophyticus* S 1517 | 209 | 0 | 0 | 0 | 0 |
| *Staphylococcus saprophyticus* S 1528 | 12 | 0 | 0 | 0 | 0 |
| *Staphylococcus schleiferi* ATCC 43808 | TNTC | 0 | 0 | 82[d] | 34[e] |
| *Staphylococcus schleiferi* ATCC 49545 | TNTC | 96 | 0[c] | TNTC[d] | TNTC[e] |
| *Staphylococcus sciuri* S 1540 | 51 | 0 | 0 | 0 | 0 |
| *Staphylococcus sciuri* S 1513 | TNTC | 0 | 0 | 0 | 0 |
| *Staphylococcus simulans* S 1519 | TNTC | 0 | 0 | 0 | 0 |
| *Staphylococcus warneri* S 1563 | 143 | 0 | 0 | 0 | 0 |
| *Staphylococcus warneri* S 1568 | TNTC | 0 | 0 | 0 | 0 |
| *Staphylococcus warneri* S 1593 | TNTC | 0 | 0 | 0 | 0 |
| *Staphylococcus warneri* S 1595 | 207 | 0 | 0 | 0 | 0 |
| *Staphylococcus warneri* S 1598 | TNTC | 0 | 0 | 0 | 0 |
| *Staphylococcus warneri* ATCC 49454 | TNTC | 0 | 0 | 0 | 0 |
| *Staphylococcus warneri* S 1557 | 18 | 18 | 0[c] | 0[d] | 0[e] |
| *Staphylococcus warneri* S 1569 | 242 | 0 | 0 | 0 | 0 |
| *Staphylococcus xylosus* ATCC 29971 | 58 | 0 | 0 | 0 | 0 |
| *Staphylococcus xylosus* PK 6b | 248 | 0 | 0 | 81[d] | 81[e] |
| *Staphylococcus xylosus* S 1529 | TNTC | 0 | 0 | 0 | 0 |
| *Staphylococcus xylosus* S 1516 | 85 | 0 | 0 | 0 | 0 |
| *Streptococcus bovis* 162K | 178 | 0 | 0 | 0 | 0 |

[a]TNTC = Too Numerous To Count
[b]NR = Not Reported
[c]Significance difference between count by Procedure B and Procedure C1
[d]Significance difference between count by Procedure B and Procedure C2
[e]Significance difference between count by Procedure B and Procedure C3

TABLE 4

Counts of *S. aureus* Pure Cultures Using Various Detection Procedures

| | Average Counts for Indicated Procedure | | | | |
|---|---|---|---|---|---|
| Organism | A | B | C1 | C2 | C3 |
| *Staphylococcus aureus* S 1508 | 86 | 67 | 83 | 70 | 91 |
| *Staphylococcus aureus* S 1514 | 74 | 52 | 55 | 51 | 54 |
| *Staphylococcus aureus* S 1520 | 181 | 178 | 199 | 195 | 183 |
| *Staphylococcus aureus* S 1522 | 47 | 49 | 57 | 64 | 47 |
| *Staphylococcus aureus* S 1527 | 54 | 34 | 36 | 28 | 43 |
| *Staphylococcus aureus* S 1537 | 159 | 133 | 112 | 99 | 120 |
| *Staphylococcus aureus* S 1538 | 59 | 45 | 48 | 51 | 39 |
| *Staphylococcus aureus* S 1552 | 77 | 79 | 59 | 50[b] | 59 |
| *Staphylococcus aureus* S 1553 | 69 | 57 | 42 | 44 | 35 |
| *Staphylococcus aureus* S 1555 | 44 | 44 | 35 | 38 | 31 |
| *Staphylococcus aureus* S 1556 | 46 | 40 | 44 | 46 | 39 |
| *Staphylococcus aureus* S 1564 | 64 | 69 | 63 | 69 | 56 |
| *Staphylococcus aureus* S 1566 | 72 | 53 | 45 | 45 | 45 |
| *Staphylococcus aureus* S 1567 | 50 | 47 | 51 | 55 | 46 |
| *Staphylococcus aureus* S 1570 | 46 | 36 | 42 | 39 | 44 |
| *Staphylococcus aureus* S 1576 | 55 | 40 | 55 | 49 | 57 |
| *Staphylococcus aureus* S 1577 | 151 | 128 | 128 | 124 | 124 |
| *Staphylococcus aureus* S 1579 | 134 | 74 | 87 | 89 | 83 |
| *Staphylococcus aureus* S 1581 | 59 | 45 | 53 | 45 | 50 |
| *Staphylococcus aureus* S 1583 | 66 | 43 | 51 | 47 | 49 |
| *Staphylococcus aureus* S 1584 | 96 | 69 | 67 | 67 | 62 |
| *Staphylococcus aureus* S 1585 | 73 | 66 | 71 | 69 | 72 |
| *Staphylococcus aureus* S 1586 | 89 | 70 | 68 | 55 | 74 |
| *Staphylococcus aureus* S 1587 | 46 | 61 | 55 | 57 | 51 |
| *Staphylococcus aureus* S 1558 | 68 | 48 | 65 | 61 | 67 |
| *Staphylococcus aureus* S 1589 | 64 | 60 | 41 | 37 | 41 |
| *Staphylococcus aureus* S 1599 | 55 | 57 | 40 | 30[b] | 44 |
| *Staphylococcus aureus* S 1600 | 75 | 58 | 47 | 53 | 42 |
| *Staphylococcus aureus* ATCC 6538 | 61 | 54 | 54 | 49 | 52 |
| *Staphylococcus aureus* ATCC 8095 | 75 | 63 | 64 | 63 | 64 |
| *Staphylococcus aureus* ATCC 9144 | 78 | 65 | 41 | 35[b] | 36[c] |
| *Staphylococcus aureus* ATCC 12598 | 41 | 44 | 59 | 50 | 64 |

TABLE 4-continued

Counts of *S. aureus* Pure Cultures Using Various Detection Procedures

| | Average Counts for Indicated Procedure | | | | |
|---|---|---|---|---|---|
| Organism | A | B | C1 | C2 | C3 |
| Staphylococcus aureus ATCC 12600 | 61 | 58 | 36 | 37 | 36 |
| Staphylococcus aureus ATCC 13301 | 51 | 35 | 44 | 41 | 47 |
| Staphylococcus aureus ATCC 13565 | 33 | 29 | 28 | 28 | 28 |
| Staphylococcus aureus ATCC 25923 | 30 | 32 | 34 | 26 | 40 |
| Staphylococcus aureus ATCC 27659 | 33 | 27 | 28 | 29 | 26 |
| Staphylococcus aureus ATCC 27660 | 38 | 23 | 24 | 19 | 24 |
| Staphylococcus aureus ATCC 27661 | 60 | 53 | 53 | 57 | 47 |
| Staphylococcus aureus ATCC 51740 | 57 | 59 | 56 | 53 | 57 |
| Staphylococcus aureus OR 1 | 16 | 23 | 13 | 9 | 14 |
| Staphylococcus aureus OR 6 | 64 | 45 | 32 | 30 | 27 |
| Staphylococcus aureus OR 12 | 13 | 10 | 9 | 5 | 7 |
| Staphylococcus aureus W 832 | 43 | 43 | 14[a] | 38 | 45 |
| Staphylococcus aureus S 1560 | TNTC | TNTC | 102[a] | TNTC | TNTC |

[a]Significance difference between count by Procedure B and Procedure C1
[b]Significance difference between count by Procedure B and Procedure C2
[c]Significance difference between count by Procedure B and Procedure C3

TABLE 5

Detection of *S. aureus* Using Procedures C2 and C3 versus Procedure B

| | Procedure B (BPA + Coagulase) | |
|---|---|---|
| | Positive | Negative |
| Procedure C2 (SEP Plate + Verification Disk) | | |
| Positive | 46 | 4 |
| Negative | 1 | 59 |
| Procedure C3 (SEP Plate + 60° C.-Heating Step + Verification Disk) | | |
| Positive | 46 | 2 |
| Negative | 1 | 61 |

TABLE 6

Counts of *S. aureus* Inoculated Into Food Samples

| | Average Counts for Indicated Procedure | | | |
|---|---|---|---|---|
| Food Sample | A | B | C1[a] | C2[b] |
| Shredded Cheese | 104 | 92 | 104 | 100 |
| Raw Beef Roast | 210 | 116 | 104 | 101 |
| Pasta Salad | 127 | 106 | 117 | 114 |
| Hashbrowns | 179 | 107 | 144 | 141 |
| Salmon | 141 | 97 | 121 | 120 |
| Custard Pastry | 179 | 162 | 176 | 172 |

[a]Red-violet colony counts only; no blue-green or black colonies observed
[b]Pink halo colony counts Example 5

Detection of *Staphylococcus aureus* Inoculated into a Food Sample

An overnight (37° C.) Tryptic Soy Broth culture of *S. aureus* ATCC strain 8095 was diluted into Tryptone Salt Buffer and an aliquot of the Buffer added to a food sample suspension such that approximately 120–160 cfu/ml were present in the sample. The inoculated food sample was then analyzed according Procedure A (PETRIFILM AC Plates; single replication), Procedure B (Baird Parker Agar; average of 6 replicates), Procedure C1 (SEP Plates without 60° C.-Heating Step and without Verification Disk; average of 2 replicates), and Procedure C2 (SEP Plates without 60° C.-Heating Step and with Verification Disk; average of 2 replicates) as described in Example 4. Results are reported in Table 6 for six different food samples and show very good correlation of *S. aureus* counts between the different test procedures.

Example 6

Detection of *Staphylococcus aureus* Naturally Occurring in a Food Sample

Two different raw milk cheese samples contaminated with *S. aureus* were analyzed according Procedure A, Procedure C1, and Procedure C2 as described in Example 4. Results are reported in Table 7 for the two food samples diluted at various levels with Tryptone Salt Buffer and adjusted as appropriate to a pH of 6.0 to 8.0. The data in Table 7 show excellent correlation between Procedures C1 (without using Verification Disk) and C2 (with Verification Disk) at the higher dilutions (1/50 and 1/100) with little or no observation of non-*S. aureus* bacteria; however, at the lower dilution (1/10) significant levels of background bacteria are evident and it becomes necessary to utilize Procedure C2 in order to obtain an accurate *S. aureus* count.

TABLE 7

Counts of S. aureus Naturally Occurring in Food Samples

| | | | Average Counts for Indicated Procedure | |
|---|---|---|---|---|
| Food Sample | Dilution | A | C1[a] Red-Violet/Black | C2[b] |
| Fourme D' Ambert | 1/10 | TNTC[c] | 0/104 | 98 |
| | 1/50 | TNTC | 18/2 | 18 |
| | 1/100 | 153 | 8/0 | 8 |
| Raw Milk Cheese | 1/10 | TNTC | 0/50 | 44 |
| | 1/50 | TNTC | 10/0 | 9 |
| | 1/100 | 288 | 7/0 | 7 |

[a]Red-violet and black colony counts; no blue-green colonies observed
[b]Pink halo colony counts
[c]TNTC = Too Numerous To Count The complete disclosures of the patents, patent documents and publications cited herein are incorporated by reference in their entirety as if each were individually incorporated. In case of conflict, the present specification, including definitions, shall control.

Various modifications and alterations to this invention will become apparent to those skilled in the art without departing from the scope and spirit of this invention. Illustrative embodiments and examples are provided as examples only and are not intended to limit the scope of the present invention. The scope of the invention is limited only by the claims set forth as follows.

What is claimed is:

1. A selective, differentiating culture medium comprising:
    a dry composition that comprises
        at least one first selective agent that selects for growth of staphylococci, the first selective agent comprising lithium chloride and aztreonam;
        at least one second selective agent for differentiating Staphylococcus aureus from other staphylococci, the second selective agent comprising potassium tellurite;
        at least one first indicator for indicating the presence of staphylococci;
        at least one second indicator for differentially indicating the presence of non-staphylococci bacteria, and egg yolk.

2. The culture medium of claim 1 wherein the first indicator comprises a phosphatase substrate that produces a detectable signal in the presence of phosphatase.

3. The culture medium of claim 2 wherein the detectable signal comprises a chemiluminescent signal, a fluorescent signal, a color change, a change in electrical conductivity, or any combination of any of the foregoing.

4. The culture medium of claim 2 wherein the first indicator comprises 5-bromo-6-chloro-3-indolylphosphate or 6-chloro-3-indolylphosphate.

5. The culture medium of claim 1 wherein the second indicator comprises 5-bromo-4chloro-3indolyl-β-D-glucopyranoside.

6. The culture medium of claim 1 further comprising a gelling agent.

7. A dry bacterial culture device comprising:
    a thin film culture plate that comprises
        a self-supporting waterproof substrate,
        a cover sheet at least partially affixed to a portion of the substrate; and
        a dry culture medium adhered to at least a portion of the substrate, a portion of the cover sheet or both, the dry culture medium comprising
            at least one first selective agent that selects for growth of staphylococci, the first selective agent comprising lithium chloride and aztreonam,
            at least one second selective agent comprising potassium tellurite for differentiating Staphylococcus aureus from other staphylococci,
            at least one first indicator for indicating the presence of staphylococci,
            at least one second indicator for differentially indicating the presence of non-staphylococci bacteria, and egg yolk.

8. The culture device of claim 7 wherein the first indicator comprises a phosphatase substrate that produces a detectable signal in the presence of phosphatase.

9. The culture device of claim 8 wherein the detectable signal comprises a chemiluminescent signal, a fluorescent signal, a color change, a change in electrical conductivity, or any combination of any of the foregoing.

10. The culture device of claim 8 wherein the first indicator comprises 5-bromo-6-chloro-3-indolylphosphate or 6-chloro-3-indolylphosphate.

11. The culture device of claim 7 wherein the second indicator comprises 5-bromo-4-chloro-3-indolyl-β-D-glucopyranoside.

12. The culture device of claim 7 further comprising a gelling agent.

13. The culture device of claim 7 wherein a first component of the culture medium is adhered to a portion of the substrate and a second component of the culture medium is adhered to a portion of the cover sheet.

14. A method of analyzing a sample for the presence or absence of Staphylococcus aureus, the method comprising:
    (a) inoculating a culture medium with a sample, the culture medium comprising at least one first selective agent that selects for growth of staphylococci comprising lithium chloride and aztreonam, at leest one second selective agent comprising potassium tellurite for differentiating Staphylococcus aureus from other staphylococci, at least one first indicator for indicating the presence of staphylococci, at least one second indicator for differentially indicating the presence of non-staphylococci bacteria, and egg yolk;
    (b) incubating the inoculated culture medium under conditions that permit growth of Staphylococcus aureus; and
    (c) inspecting the culture medium to determine whether Staphylococcus aureus is present.

15. The method of claim 14 wherein the culture medium comprises a liquid medium, a semi-solid medium, a solid medium, or a reconstituted dry culture medium.

16. The method of claim 14 wherein incubating the inoculated culture medium under conditions that permit growth of Staphlylococcus aureus comprises incubating the inoculated culture medium for at least about 18 hours at about 30° C. to about 42° C.

17. The method of claim 16 wherein the inoculated culture medium is incubated for from about 18 hours to about 48 hours.

18. The method of claim 17 wherein the inoculated culture medium is incubated for about 24 hours.

19. The method of claim 16 wherein the inoculated culture medium is incubated at about 37° C.

20. The method of claim 14 wherein the first indicator comprises a phosphatase substrate that produces a detectable signal in the presence of phosphatase.

21. The method of claim 20 wherein the detectable signal comprises a chemiluminescent signal, a fluorescent signal, a color change, a change in electrical conductivity, or any combination of any of the foregoing.

22. The method of claim 20 wherein the first indicator comprises 5-bromo-6-chloro-3-indolylphosphate or 6-chloro-3-indolylphosphate.

23. The method of claim 22 wherein inspecting the culture medium to determine whether *Staphylococcus aureus* is present comprises detecting red colonies.

24. The method of claim 14 further comprising enumerating *Staphylococcus aureus* colonies.

25. A method of detecting thermonuclease-positive staphylococci, the method comprising:
    (a) providing a culture medium selective for growing staphylococci, the culture medium comprising lithium chloride, aztreonam, potassium tellurite and egg yolk;
    (b) inoculating the culture medium with a sample;
    (c) incubating the inoculated culture medium under conditions effective to promote the growth of staphylococci;
    (d) providing an indicator system that produces a differentiable, detectable signal in the presence of thermonuclease-positive staphylococci;
    (e) contacting the indicator system with the inoculated, incubated culture medium, thereby forming a detection assembly;
    (f) incubating the detection assembly under conditions effective for generating the differentiable, detectable signal; and
    (g) detecting the presence of thermonuclease-positive staphylococci by the presence of a detectable signal;
    wherein the detection assembly is maintained at temperatures less than about 60° C. at least until the detectable signal is detected.

26. The method of claim 25 wherein the detection assembly is maintained at temperatures less than about 42° C. at least until the detectable signal is detected.

27. The method of claim 25 wherein incubating the inoculated culture medium under conditions effective to promote growth of *Staphylococcus aureus* comprises incubating the inoculated culture medium for at least about 16 hours at about 30° C. to about 42° C.

28. The method of claim 27 wherein the inoculated culture medium is incubated for from about 18 hours to about 48 hours.

29. The method of claim 28 wherein the inoculated culture medium is incubated for about 24 hours.

30. The method of claim 27 wherein the inoculated culture medium is incubated at about 37° C.

31. The method of claim 28 wherein incubating the detection assembly under conditions effective for generating a detectable signal comprises incubating the detection assembly at from about 4° C. to about 42° C.

32. The method of claim 31 wherein the detection assembly is incubated at about 37° C.

33. The method of claim 25 wherein incubating the detection assembly under conditions effective for generating a detectable signal comprises incubating the detection assembly for about 1 minute to about 48 hours.

34. The method of claim 33 wherein the detection assembly is incubated for about 1 hour to about 3 hours.

35. The method of claim 25 wherein the indicator system comprises toluidine blue O.

36. The method of claim 35 wherein the indicator system further comprises unhydrolyzed nucleotides.

37. The method of claim 36 wherein detecting the detectable signal comprises detecting colonies with pink halos.

38. The method of claim 25 further comprising enumerating colonies of thermonuclease-positive staphylococci.

39. A kit for detection and enumeration of *Staphylococcus aureus*, the kit comprising:
    (a) nutrients effective for growing staphylococci from a sample;
    (b) reagents comprising lithium chloride and aztreonam that select for growth of staphylococci; and
    (c) at least one indicator for indicating the presence of *Staphylococcus aureus*.

40. The kit of claim 39 wherein the reagents further comprise potassium tellurite and egg yolk.

41. The kit of claim 39 wherein the indicator comprises a phosphatase substrate.

42. The kit of claim 41 wherein the indicator comprises 5-bromo-6-chloro-3-indolylphosphate or 6-chloro-3-indolylphosphate.

43. A method of detecting thermonuclease-positive staphylococci, the method comprising:
    (a) providing the culture medium of claim 1;
    (b) inoculating the culture medium with a sample;
    (c) incubating the inoculated culture medium under conditions effective to promote the growth of staphylococci;
    (d) providing an indicator system that produces a differentiable, detectable signal in the presence of thermonuclease-positive staphylococci;
    (e) contacting the indicator system with the inoculated, incubated culture medium, thereby forming a detection assembly;
    (f) incubating the detection assembly under conditions effective for generating the differentiable, detectable signal; and
    (h) detecting the presence of thermonuclease-positive staphylococci by the presence of a detectable signal.

44. The method of claim 43, wherein the detection assembly is maintained at temperatures less than about 60° C. at least until the detectable signal is detected.

45. The method of claim 43 wherein the detection assembly is incubated for about 1 hour to about 3 hours.

46. The method of claim 43 wherein the detection assembly is incubated at about 37° C.

47. The method of claim 43 wherein the indicator system comprises toluldine blue O and unhydrolyzed nucleotides.

48. The method of claim 43 further comprising enumerating colonies of thermonuclease-positive staphylococci.

* * * * *

UNITED STATES PATENT AND TRADEMARK OFFICE
CERTIFICATE OF CORRECTION

PATENT NO. : 7,087,401 B2
APPLICATION NO. : 10/177420
DATED : August 8, 2006
INVENTOR(S) : Gregory P. Sandberg It is certified that error appears in the above-identified patent and that said Letters Patent is hereby corrected as shown below:

Column 1
Line 39, Delete "a typical" and insert in place thereof -- atypical --;

Column 1
Line 59, Delete "et." and insert in place thereof -- et --;

Column 3
Line 60, Delete "FIGURES" and insert in place thereof -- FIGURE --;

Column 4
Line 27, Delete "an" and insert in place thereof -- on --;

Column 19
Line 56-57, In Claim 5, delete "5-bromo-4chloro-3indolyl-ß-D-glucopyranoside." and insert in place thereof -- 5-bromo-4-chloro-3indolyl-ß-D-glucopyranoside. --;

Column 19
Line 66, In Claim 7, after the word "sheet" insert -- , --;

Column 20
Line 36, In Claim 14, after the word "at" delete "leest" and insert in place thereof -- least --;

Column 20
Line 53, In Claim 16, delete "Staphlylococcus" and insert in place thereof -- Staphylococcus --;

Column 21
Line 42, In Claim 27, after the word "about" delete "16" and insert in place thereof -- 18 --;

UNITED STATES PATENT AND TRADEMARK OFFICE
CERTIFICATE OF CORRECTION

PATENT NO.        : 7,087,401 B2
APPLICATION NO.   : 10/177420
DATED             : August 8, 2006
INVENTOR(S)       : Gregory P. Sandberg It is certified that error appears in the above-identified patent and that said Letters Patent is hereby corrected as shown below:

Column 22
Line 55, In Claim 47, delete the word "toluldine" and insert in place thereof
-- toluidine --.

Signed and Sealed this

Twenty-sixth Day of December, 2006

JON W. DUDAS
*Director of the United States Patent and Trademark Office*